United States Patent
Shoher et al.

(10) Patent No.: US 6,848,898 B2
(45) Date of Patent: Feb. 1, 2005

(54) ADAPTATION DEVICE FOR MOLDING A DENTAL MATERIAL

(76) Inventors: Itzhak Shoher, 50 Shlomo Hamelechst, Tel Aviv (IL), 64386; Ahqron Whiteman, J.L. Peretz St. 13, Petach Tikvah (IL), 49206

( * ) Notice: Subject to any disclaimer, the term of this patent is extended or adjusted under 35 U.S.C. 154(b) by 695 days.

(21) Appl. No.: 09/941,825

(22) Filed: Aug. 29, 2001

(65) Prior Publication Data

US 2004/0004302 A1 Jan. 8, 2004

(51) Int. Cl.⁷ .......................... B29C 53/36; A61C 13/20
(52) U.S. Cl. ....................................... 425/405.1; 249/54
(58) Field of Search ................................ 425/110, 175, 425/405.1, 405.2; 249/54

(56) References Cited

U.S. PATENT DOCUMENTS

| | | | | |
|---|---|---|---|---|
| 1,689,533 A | * | 10/1928 | Parker ............................. | 264/86 |
| 2,030,524 A | * | 2/1936 | Lambert ........................ | 425/175 |
| 2,222,531 A | * | 11/1940 | Dwyer ........................... | 425/175 |
| 2,333,295 A | * | 11/1943 | Chevigny ...................... | 315/39 |
| 3,277,576 A | * | 10/1966 | Kraft .............................. | 433/53 |
| 3,286,350 A | * | 11/1966 | Cooper .......................... | 433/74 |
| 3,618,179 A | * | 11/1971 | Anderson et al. ............ | 425/405.2 |
| 4,056,585 A | * | 11/1977 | Waltke .......................... | 433/74 |
| 4,349,326 A | * | 9/1982 | Foster et al. ................ | 425/405.1 |
| 5,234,343 A | * | 8/1993 | Shoher et al. ............... | 433/215 |
| 5,302,104 A | * | 4/1994 | Ueda ............................. | 425/178 |
| 5,593,305 A | * | 1/1997 | Shoher et al. ............... | 433/218 |
| 5,730,600 A | * | 3/1998 | Shoher et al. ............... | 433/223 |
| 6,082,141 A | * | 7/2000 | Kuster .......................... | 65/289 |
| 6,506,054 B2 | * | 1/2003 | Shoher et al. ............... | 433/223 |

* cited by examiner

Primary Examiner—Tim Heitbrink

(57) ABSTRACT

An adaptation device and method for molding a dental material to a die in the preparation of a dental coping with the die having the shape of a tooth to be restored and with said dental material placed over said die. The adaptation device includes a base for placement of the die, a cover mounted on the base over the die to form an enclosed chamber, an inlet opening extending through the cover into communication with the chamber, a source of a gaseous fluid connected to the inlet opening for pressurizing the chamber, an outlet opening extending through the base in proximity to said die and diaphragm means removably positioned in the chamber to surround the die and to isolate the outlet opening from the chamber such that upon pressurizing the chamber the diaphragm is caused to collapse about the die and to apply a uniform pressure over the dental material for adapting the dental material to the die.

13 Claims, 1 Drawing Sheet

ADAPTATION DEVICE FOR MOLDING A DENTAL MATERIAL

FIELD OF THE INVENTION

This invention relates to an adaptation device and method for molding dental material to a die in the preparation of a dental coping.

BACKGROUND OF THE INVENTION

In crown and bridge prosthodontics, dental copings of metal are conventionally used to provide the essential structural strength and rigidity necessary for a dental restoration to resist the forces of mastication when food is eaten. In a ceramic-to-metal dental restoration, the metal coping forms the understructure of a dental crown and/or a bridge, over which is applied a fired-on coating of porcelain or a polymer based veneering material.

A metal coping may be cast from an investment of a wax or plastic pattern of the tooth to be restored. An alternative procedure for forming a precious metal coping which does not require waxing, investing or casting has currently been gaining wide acceptance in the dental profession by both dentists and dental laboratories. This alternative procedure requires the use of a moldable material composition formed from a base material composition of high and low fusing temperature metal particles and a binder preferably of dental wax as is disclosed, for example, in U.S. Pat. Nos. 5,234,343, 5,593,305 and 5,730,600 respectively, each disclosure of which is herein incorporated by reference.

In accordance with the teaching of the aforementioned patents the moldable material is hand molded over a die which has the shape of the tooth to be restored. The heat treating temperature must be above the melting temperature of the low fusing temperature metal particles of the moldable material and below the melting temperature of the high fusing temperature metal particles. Heat treatment transforms the hand molded structure into a porous metallic shell having the same shape as before heat treatment without suffering any significant shrinkage. The wax in the molded material vaporizes during heat treatment leaving the porous metallic shell with a high void volume of preferably above at least 20%. A filler material of metal or ceramic is melted into the porous shell to densify and solidify the shell into the dental coping over which may be applied a fired-on coating of porcelain or a polymer based veneering material for aesthetics. The filler material is preferably of a precious metal such as gold or a gold alloy in a wax binder.

The geometry of the base and filler materials are currently made available to the dental laboratory in the form of thin compacted strips of rectangular geometry. The hand molding operation is a procedure in which the conventional strip of base material is cut into separate pieces each of which is separately applied to the die by hand followed by hand pressing the pieces against the die. A hand burnishing tool may be used to assist the technician. This procedure of hand pressing the material to hand mold it to the surface of the die is time consuming and labor intensive. During the formation of the coping the filler material may be added to the molded structure either in a secondary heat treatment operation or during the primary heat treatment of the coping shell.

The objective of the present invention is to provide an adaptation device and method to assist the laboratory technician or dentist in molding dental material to the die before heat treatment so as to minimize the labor intensive characteristic of the procedure and to substantially increase the speed of forming a mold while assuring uniformity in the quality of the molded structure.

SUMMARY OF THE INVENTION

The adaptation device of the present invention will mold a dental material to a die in the preparation of a dental coping with the die having the shape of a tooth to be restored and with said dental material placed over said die. The adaptation device comprises; a base for placement of the die, a cover mounted on the base to form an enclosed chamber spaced over the die, an inlet opening extending through said cover into communication with said chamber, a source of a pressurized fluid connected to said inlet means, an outlet opening extending through said base in proximity to said die and diaphragm means surrounding die so as to form a secondary chamber with said outlet opening isolated from said chamber such that upon pressurizing said chamber with said gaseous fluid said diaphragm is caused to collapse about said die and to apply a uniform pressure over said dental material for adapting said dental material to the die.

In the method of the present invention a dental material is prepared for adaptation to a die having the shape of a tooth to be restored in the preparation of a dental coping comprising the steps of placing the dental material on the die to which it is to be adapted, enclosing the die and dental material in a plenum chamber of a housing having an inlet opening adapted to be connected to a source of fluid for pressuring the chamber and an outlet opening extending into the housing in proximity to the die, mounting an elastic member over said die and said dental material to isolate the outlet opening from the plenum chamber and pressuring the plenum chamber to cause said diaphragm to collapse about said die for uniformly applying pressure to adapt said dental material to the die.

BRIEF DESCRIPTION OF THE DRAWINGS

Additional advantages of the present invention will become apparent from the following detailed description of the invention when read in conjunction with the accompanying drawings of which.

DETAILED DESCRIPTION OF THE INVENTION

Figure 1:
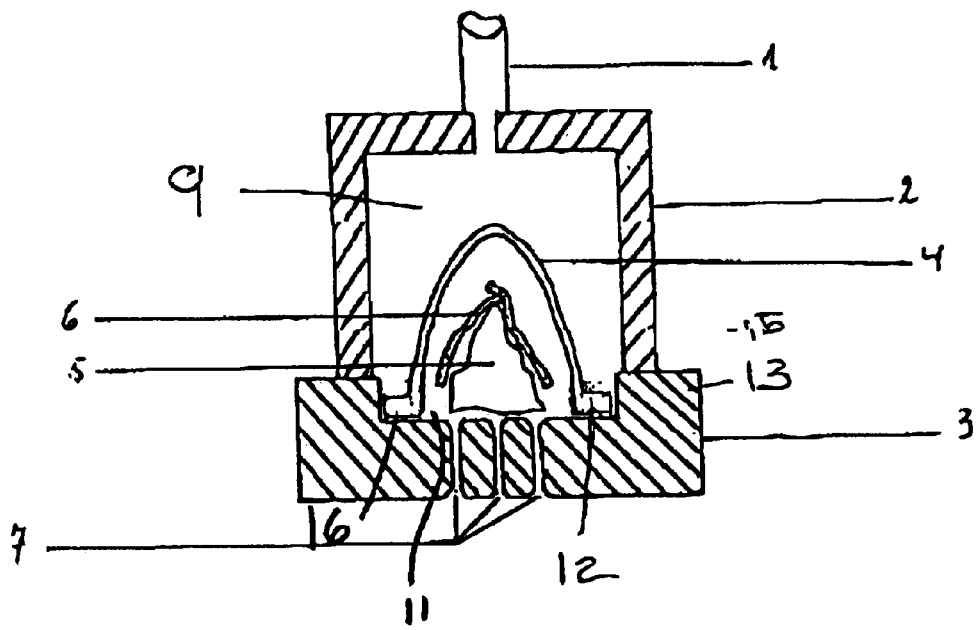
FIG. 1 is a cross sectional view of the device of the present invention showing the die and dental composition in a position within a plenum chamber surrounded by an elastic member before the chamber is pressurized.

The adaptation device 10 of the present invention comprises a base 3, a removable cover 2 mounted on the base 3 for forming an enclosed primary chamber 9, at least one inlet opening 14 extending through the cover 2 in communication with the primary chamber 9 and one or more outlet passageways 7 extending through the base 3. A tube 1 is connected to a source (not shown) of pressurized fluid such as air which is affixed to the inlet opening for pressurizing the primary chamber 9. The base 3 has an annular upright shoulder 13 forming a recessed area 11. A refractory or other conventional dental die 5 is mounted upon the base 3 within the recessed area 11. The outlet passageways 7 preferably lead into the recessed area 11 in proximity to the die 5 and face the underside of the die 5. The cover 2 and base 3 of the adaptation device 10 may be of any desired geometry preferably circular or rectangular.

An elongated tubular member 4 of an elastic material composition having one open end 16 is mounted with the open end 16 seated on the base 3 to form a secondary chamber 15 between the die 5 and the member 4 which is in communication with the outlet passageways 7. The tubular elastic member 4 surrounds the die 5 and isolates the secondary chamber 15 and die 5 from the primary chamber 9. The tubular elastic member 4 functions as a diaphragm and may be composed of any elastomeric material composition such as a resinous plastic or rubber. The open end 16 of the tubular elastic member 4 when seated on the base 3 forms a flange extending outwardly toward upright shoulder 13 which enables the tubular elastic member 4 to stand upright and be self supporting on the base 3 and to seal off the secondary chamber 15 from the primary chamber 9. A removable clamp 12 may be mounted over the open end 16 of the elastic member 4 to hold it in place to assure the formation of a seal between the secondary chamber 15 and the primary chamber 9 when the primary chamber 9 is pressurized. The clamp 12 may, if necessary, be spring loaded. The removable clamp is however optional and in many cases will not be needed.

Figure 2:
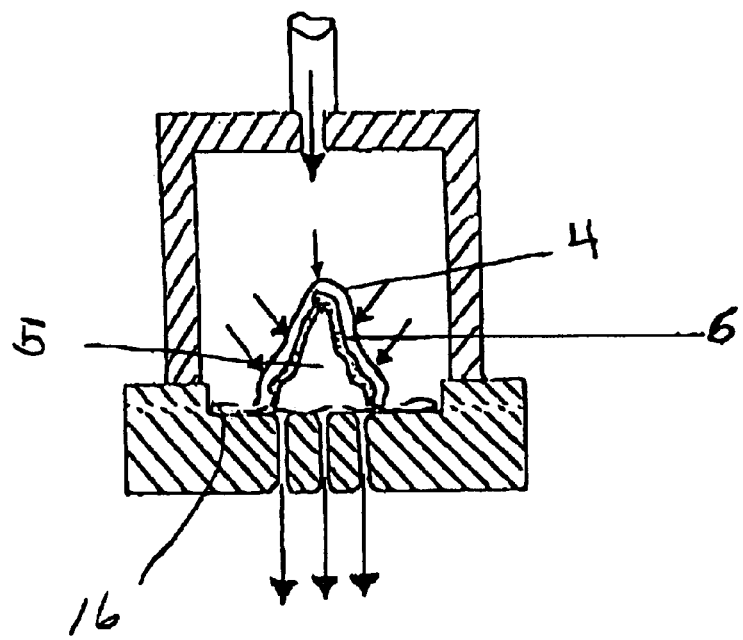
FIG. 2 is another cross sectional view of the device of the present invention after the chamber is pressurized.

Dental material 6 is first mounted over the outer surfaces of the die 5 with the cover 2 removed and before placement of the tubular elastic member 4 on the base 3. Thereafter the primary chamber 9 is pressurized by injecting a gaseous fluid such as air fed from a supply source (not shown) into the chamber 9 at a predetermined pressure. This causes the surrounding tubular elastic member 4 to collapse over the die 5 and forces air to discharge from the secondary chamber 15 through the passageways 7 into the atmosphere external of the device 10. A uniform pressure is applied to the dental material 6 so as to adapt i.e. mold the dental material to the die 5 thereby forming a molded structure having the shape of the die 5. Alternatively and/or simultaneously, a vacuum may be drawn in the secondary chamber 15 through the pasageways. As is shown in FIG. 2 once the tubular elastic diaphragm 4 collapses around the die 5 the dental material 6 is squeezed against the die 5 molding it to the surface of the die 5.

The dental material 6 may be a base material composed of metal particles formed, preferably, from a mixture of high- and low-fusing temperature metal particles and a volatile binder of preferably wax. Upon heat treatment, the binder will vaporize to leave a porous, sponge-like structure having a capillary network of multiple voids uniformly distributed throughout the structure, with a void volume preferably of at least twenty percent (20%), and up to eighty percent (80%).

The preferred binder is composed substantially or entirely of wax, with the remainder, if any, of an organic or hydrocarbon compound to control the malleability of the dental material. The term "wax," for purposes of the present invention, means any natural wax, mineral wax, or organic wax, or combination thereof. The concentration of the binder is preferably high enough to assure a void volume of at least twenty percent (20%). When the concentration of binder is at least twenty percent (20%) by volume, the relationship between void volume and binder is substantially one-to-one.

In accordance with the present invention, a filler material may be melted into the voids of the heat-treated porous structure to solidify the structure for forming the dental coping of the present invention. The filler material may be any suitable ceramic or metal composition, preferably a precious metal composition. The filler material may also be formed of a matrix of particles mixed with a wax binder having a composition and concentration similar to the composition and concentration of the binder used to form the porous structure. A minimum binder concentration of at least about twenty percent (20%) by volume is preferred, and up to eighty-five percent (85%) by volume. Fifty percent (50%) or more of the overall weight of the filler composition is preferably of individual or alloyed particles, of any size, containing between 90% to 98.5% gold with the remainder preferably selected from the third or fourth groups of elements of the periodic table.

The high-fusing temperature metal particles may be of a single metal or metal alloy, preferably of precious metals such as platinum and/or palladium, in any desired proportion relative to each other, from zero to one hundred percent, with or without other constituents such as gold, silver, copper, magnesium, aluminum, zinc, gallium, indium, and other metals or elements from the third, fourth, or fifth group of elements of the periodic table. Gold may be added to the high-fusing temperature metal particles to increase the affinity of the high-fusing temperature metal particles to the low-fusing temperature metal particles, or to itself in the absence of low-fusing metal particles. In the latter instance, gold may represent the major constituent of the high-fusing metal component of the base material, and, depending on its concentration, will form a composition which may melt, or at least partially melt, at a temperature as low as 900–950° C. to permit the particles to join.

The heat treatment must eliminate the binder, preferably without leaving a residue, and cause the low-fusing particles, if present, to melt to form a stable porous metal structure with a twenty (20%) to eighty percent (80%) void volume and a uniformly distributed void matrix. The void volume will substantially correspond in percent to the percent concentration of binder before heat treatment, provided it is above the minimum concentration of twenty percent (20%).

In accordance with the preferred embodiment of the present the dental material 6 may have any geometrical shape. If the shape of the dental material is, for example, a rectangular sheet as is currently conventional pieces may be cut out from the sheet and arbitrarily placed on the die 5 to cover its entire surface i.e. not to leave exposed surface areas. If surface tension is not sufficient of itself to hold the dental pieces in place any conventional adhesive composition or tacky material in paste, liquid or gel form, preferably with a wax additive which will volatize during heat treatment, may be used as a surface treatment for the die 5 for the purpose of simplifying the placement and attachment of the dental material 6 to the surface of the die 5. Placing the pieces of dental material 6 over the die 5 may result in overlapping seams at adjoining surfaces or ends which may, in some instances, be desirable. Any number of pieces may be used including a single piece if its geometrical shape conforms somewhat to the shape of the die 5. The latter may be accomplished by forming the dental material into a three dimensional shape having a geometry substantially conforming to the surface geometry of the die 5 as taught in Applicants copending application Ser. No. 09/811,453, filed on Mar. 20, 2001, which is incorporated herein by reference. The thickness of the dental material 6 from which the pieces are cut is not significant to the invention but should generally be between twenty-five (25) microns and ten (10) millimeters thick.

To cause the dental material 6 to form a unitary molded structure in preparation for heat treatment the primary chamber 9 should preferably be pressurized at a pressure of between 2–7 atmospheres. Although the pressure is uniformly applied the molded structure may still possess overlapping seams which may be considered too thick. Accordingly, before heat treatment a spatula or other hand tool may be used to smooth out the overly thick areas as is currently practiced. After the dental material 6 is adapted to the die 5 the chamber 9 can be depressurized and the diaphragm 4 removed from the surface of the die. Upon depressurization the diaphragm 4 will return to its normal shape before depressurization.

The filler material may be added after heat treatment or may be molded over the die at the same time. In fact, the dental material may represent a dual laminate of base and filler materials or may constitute separate sheets of base and filler material. The heat treatment of the filler material may also be done in a furnace or using a flame at a temperature generally below the heat-treatment temperature, substantially equal to, or slightly above the first heat-treatment temperature.

The usual heat-treatment temperature range for the dental material is between 800° C. and 1200° C. Once the metal coping is formed, a conventional porcelain or acrylic veneer may be applied thereover to form a conventional ceramic-to-metal dental restoration.

What is claimed:

1. An adaptation device for molding a dental material to a die in the preparation of a dental coping with the die having the shape of a tooth to be restored and with said dental material placed over the surface of said die before the dental matrial is adapted to the die, said adaptation device comprising; a base for placement of the die, a cover mounted on the base over the die to form an enclosed primary chamber, an inlet opening extending through said cover into communication with said primary chamber, a source of gaseous fluid connected to said inlet opening for pressurizing said primary chamber, one or more outlet opening(s) extending through said base in proximity to said die and diaphragm means surrounding said die and said outlet opening(s) for isolating said die from said primary chamber such that upon pressurizing said primary chamber with said gaseous fluid said diaphragm is caused to collapse about said die and apply a uniform pressure over said dental material composition for adapting said dental material to the die.

2. An adaptation device as defined in claim 1 wherein said diaphragm means is a tubular elastic member having one open end mounted on said base to form a secondary chamber which communicates with the outlet opening(s) with said open end sealing off said secondary chamber from said primary chamber.

3. An adaptation device as defined in claim 2 wherein said tubular elastic member is composed of a polymeric composition or of a natural rubber.

4. An adaptation device as defined in claim 3 further comprising a removable clamp mounted over the open end of said tubular elastic member to assure the formation of a seal between said secondary chamber and said primary chamber.

5. An adaptation device as defined in claim 3 wherein said base further includes a recessed area upon which the die is mounted.

6. An adaptation device as defined in claim 5 wherein said outlet opening(s) extend through said base to a location in said recessed area facing the underside of said die.

7. An adaptation device as defined in claim 6 wherein said primary chamber is pressurized to between 2–7 atmospheres.

8. An adaptation device as defined in claim 7 wherein said gaseous fluid is air.

9. An adaptation device as defined in claim 6 wherein the secondary chamber has a vacuum.

10. An adaptation device as defined in claim 6 wherein said dental material is composed of a base composition comprising high and low fusing temperature metal particles selected from one or more precious metals or precious metal alloys and a binder.

11. An adaptation device as defined in claim 10 wherein said binder is a wax.

12. An adaptation device as defined in claim 11 wherein said dental material is composed of a mutilayer of a base material and/or a multilayer filler material.

13. An adaptation device as defined in claim 12 wherein said filler material comprises gold.

* * * * *